United States Patent [19]

Bahrmann et al.

[11] Patent Number: 5,451,698
[45] Date of Patent: Sep. 19, 1995

[54] PROCESS FOR THE PREPARATION OF SULFONATED ARYLPHOSPHINES

[75] Inventors: Helmut Bahrmann, Hamminkeln; Peter Lappe, Dinslaken; Wolfgang A. Herrmann, Freising; Rainer Manetsberger, Landshut; Guido Albanese, München; Klaus Bergrath, Oberhausen, all of Germany

[73] Assignee: Hoechst Aktiengesellschaft, Germany

[21] Appl. No.: 264,720

[22] Filed: Jun. 23, 1994

[30] Foreign Application Priority Data

Jun. 29, 1993 [DE] Germany ............ 43 21 512.2
Dec. 23, 1993 [DE] Germany ............ 43 44 066.5

[51] Int. Cl.6 ............................................ C07C 309/32
[52] U.S. Cl. ................................................... 562/35
[58] Field of Search ........................................ 562/35

[56] References Cited

FOREIGN PATENT DOCUMENTS 1471265 4/1977 United Kingdom ....... C07C 143/36

*Primary Examiner*—Nicky Chan
*Attorney, Agent, or Firm*—Jordan B. Bierman; Bierman and Muserlian

[57] ABSTRACT

The sulfonation of arylphosphines, i.e. mono-, di-, oligo- and polyphosphines, which contain at least one aromatic radical capable of being sulfonated, is carried out in the presence of a Lewis acid at 0° to 80° C. The process avoids side-reactions, in particular the formation of phosphine oxides. In treating the sulfonation mixture, the Lewis acid can be removed together with the sulfuric acid.

21 Claims, No Drawings

PROCESS FOR THE PREPARATION OF SULFONATED ARYLPHOSPHINES

The invention relates to a process for preparing sulfonated arylphosphines by reaction of arylphosphines with $SO_3/H_2SO_4$, i.e. a solution of sulfur trioxide in concentrated sulfuric acid (oleum). The novel process avoids side-reactions, in particular the formation of phosphine oxides.

BACKGROUND OF THE INVENTION

Complex compounds which contain, as their central atoms, metals of Group VIII A of the Periodic Table (IUPAC version), P(III) compounds such as phosphines as ligands, and optionally further groups capable of complex formation, have in recent years gained increasing importance as catalysts. Thus, the reaction of olefins with synthesis gas to give aldehydes (hydroformylation), which is practiced on a large scale in industry, is carried out in the presence of catalysts which comprise cobalt and particularly rhodium and triphenylphosphine. In accordance with the solubility of these catalysts in organic media the reaction proceeds in a homogeneous phase.

This reaction, like other stoichiometric and catalytic reactions, can also be carried out in heterogeneous reaction systems. This original development is not limited to complex compounds of metals of group VIII A, but also includes complex compounds of groups VII A and I B of the Periodic Table (IUPAC version) as catalysts. The use of catalysts dissolved in water permits them to be separated from the water-insoluble reaction product simply and gently.

For example, the process described in DE-C-27 00 904 for the addition of hydrogen cyanide to an unsaturated organic compound having at least one ethylenic double bond is carried out according to this principle. Suitable catalysts for this reaction are nickel/TPPTS [TPPTS is tris(m-sulfophenyl)phosphine], palladium/TPPTS or iron/TPPTS. According to DE-C-26 27 354, aldehydes are prepared by reaction of olefins with carbon monoxide and hydrogen using rhodium as metal or in the form of one of its compounds, together with a water-soluble phosphine (for example TPPTS), as the catalyst. Further catalysts of the type mentioned and their use in various reactions such as hydrogenations, allene/alkyne coupling, and amine addition to double bonds are the subject of, for example, EP-A-372 313.

Sulfonated phenylphosphines can be obtained by the process described in J. Chem. Soc., 1958, pages 281–282 by reacting triphenylphosphine with oleum, heating the reaction mixture in a water bath, diluting the reaction product with water, and neutralizing with sodium hydroxide. The sodium salt of m-sulfophenyldiphenylphosphine crystallizes from the sulfonation mixture.

Similar processes are also used to obtain disodium salts of di(m-sulfophenyl)phenylphosphine and tri(m-sulfophenyl)phosphine. The starting material in both cases is again triphenylphosphine which is reacted with oleum at temperatures between 18° and 40° C. for from 15 to 63 hours. The reaction product is diluted with water and neutralized with sodium hydroxide, care having to be taken that, during the addition of the sodium hydroxide, the temperature of the mixture is maintained below 20° C. (DE-C-26 27 354). Apart from monophosphines, sulfonated di- and polyphosphines are also used as components of catalysts. Examples of the preparation thereof are given in DE-A-40 40 314.

A disadvantage of all known processes for obtaining sulfonated arylphosphines is the undesired formation of phosphorus/oxygen compounds, i.e. the oxidation of the trivalent phosphorus to the pentavalent form by the sulfur trioxide. The resulting phosphine oxides do not form catalytically active complex compounds with metal ions, and are thus worthless as catalyst components. They are therefore customarily selectively removed from the mixture of the sulfonation products, so as not to excessively burden the catalyst solution with inert materials. To limit the oxidation, the sulfonation is carried out at temperatures which are as low as possible. This measure leads to the formation of water-soluble phosphines in which the maximum possible degree of sulfonation and thus the highest solubility in water—which is important for the retention of the metal component of the catalyst system in the water—are not achieved. More extensive sulfonation by increasing the reaction time has the drawback that the oxidation simultaneously increases.

SUMMARY OF THE INVENTION

It is, therefore, an object of the invention to develop a process which suppresses the oxidation which accompanies the sulfonation of the phosphines used, thus allowing higher reaction temperatures, longer reaction times, and the use of more concentrated oleum; hence the formation of highly sulfonated products is promoted.

The invention provides a process for preparing sulfonated arylphosphines by sulfonation of aryl-containing mono-, di-, oligo-or polyphosphines with oleum. It comprises carrying out the sulfonation at temperatures between 0° and 80° C. in the presence of Lewis acids.

It has surprisingly been found that the addition of a Lewis acid to the sulfonation mixture effectively prevents the formation of phosphine oxides. The sulfonation can therefore be carried out at a higher temperature and/or over a longer period of time, thus achieving the desired higher degree of sulfonation. Furthermore, selective removal of phosphine oxides contained in the reaction mixture becomes unnecessary in most cases.

DETAILED DESCRIPTION OF THE INVENTION

Those skilled in the art are familiar with the term "Lewis acids". These are molecules or ions which act as electron acceptors. For use in the process of the invention, they are limited to those which are stable in the sulfonating agent and under the sulfonation conditions. Examples of suitable Lewis acids are boron halides, boric acid, and halides of aluminum, phosphorus, antimony, arsenic, iron, zinc, and tin. Compounds which have proven particularly suitable in the novel process are boron compounds, preferably boric acid which is a readily available, cheap, and nontoxic material.

The Lewis acid is used in about equimolar amounts based on the P(III) atoms contained in the phosphine to be sulfonated. A slightly lower amount does no harm, but an excess is preferred. When boric acid is used as the Lewis acid, it is particularly advantageous to dissolve it in the oleum to the saturation point. The Lewis acids can be a single compound or a mixture of various compounds.

Starting compounds for the sulfonation are arylphosphines. This general designation comprehends mono-, di-, oligo-, and polyphosphines which contain at least one aromatic radical capable of being sulfonated. The aromatic radical can comprise one or more benzene rings which, as in biphenyl, are connected by a single carbon-to-carbon bond. Alternatively, they may have a plurality of common atoms in their carbon rings (condensed ring systems), for example, in the naphthyl group. The aromatic radicals can furthermore be singly or multiply substituted by chlorine, fluorine, alkyl, alkoxy, nitro, etc. Examples of monophosphines which can be sulfonated according to the novel process are dimethylphenyl-, methyldiphenyl- and triphenylphosphine. Examples of the diphosphine compounds are 2,2'-bis(diphenylphosphinomethyl)biphenyl and 2,2'-bis(diphenylphosphinomethyl)-1,1'-binaphthyl. For the purposes of the present invention, phosphines also include compounds of trivalent phosphorus in which the phosphorus atom is part of a ring system. Examples of these classes of compounds are phosphorin substituted by aromatic radicals, and also aryl- and/or alkyl-substituted phospholes and phosphanorbornadienes.

The sulfonation according to the process of the invention can be applied to arylphosphines in commercial form or in the form obtained by synthesis. Special purification is unnecessary unless the use of the sulfonated compounds as a catalyst component requires it. The sulfonating agent used is oleum having an $SO_3$ concentration of 20% to 65% by weight; the Lewis acid has advantageously already been added before the introduction of the arylphosphine. The phosphine is added to the solution while maintaining a temperature from $-5°$ to $+50°$ C., preferably from $0°$ to $+40°$ C. To avoid local overheating, it is best to insure a rapid and uniform distribution of the phosphorus compound in the sulfonating agent, e.g. by stirring.

Instead of being added as such, the phosphine is preferably mixed with the oleum as a solution in concentrated sulfuric acid, advantageously by portionwise adding the oleum while stirring to the solution which also contains the Lewis acid. The molar ratio of $SO_3$ to phosphine depends on the desired degree of sulfonation. The higher the amount of available $SO_3$ under otherwise identical reaction conditions, the more sulfonic acid groups are introduced into the phosphine molecule. The actual sulfonation reaction, which follows the dissolution of the phosphine in the oleum, is carried out at temperatures between $0°$ and $80°$ C., preferably between $10°$ and $50°$ C., likewise with continuous stirring to maintain the temperature in the reaction mixture as uniform as possible.

The reaction time can be limited to a few minutes; usually, it is from a number of hours to a number of days, in special cases even a number of weeks. Raising the reaction temperature and lengthening the reaction time lead, for the same amount of available $SO_3$, to increased sulfonation of the aryl radicals of the phosphine molecule. It is worth emphasizing that addition of Lewis acids to the sulfonation mixture in accordance with the invention allows substantially free selection of the determinative reaction parameters, in particular $SO_3$ concentration, temperature, and reaction time, within the limits given above. This is because undesired secondary oxidation is virtually absent. In this context, it has proven useful to monitor the progress of the sulfonation analytically to match the reaction parameters to one another for optimization of the reaction. A suitable sensitive and powerful method for this is $^{31}P$-NMR spectroscopy which makes possible the easy differentiation of tertiary phosphines and the phosphine oxides derived therefrom in the reaction mixture.

As soon as the reaction is complete, the reaction mixture is diluted with water and the desired product recovered. There are various methods available for this purpose. According to one known procedure, the diluted sulfuric acid solution is first neutralized. Both in the dilution and also in the neutralization, care should be taken to insure that the reaction mixture does not overheat; it has proven useful to maintain temperatures from $0°$ to $40°$ C., in particular from $0°$ C to $20°$ C. The neutralization is carried out using an aqueous solution of an alkali metal hydroxide, preferably sodium hydroxide. Alkali metal hydroxide concentrations of from 20% to 60% by weight, based on the solution, have proven useful.

To remove the alkali metal sulfate formed from sulfuric acid and alkali metal hydroxide as completely as possible, it is recommended that the dilution be not too great. Alkali metal sulfate separates out from the neutralized reaction mixture; it is then filtered out and washed a number of times with a lower alcohol, preferably a $C_1$- to $C_4$-alcohol; especially preferred is methanol. The sulfonated arylphosphine is isolated from the filtrate by removal of the water under gentle conditions, for example by distillation in an oil pump vacuum. For purification, the crystalline product obtained is redissolved in a little water, the solution is admixed with a lower alcohol, preferably a $C_1$- to $C_4$- alcohol (methanol in particular), filtered, and the solvent is again gently removed.

According to a preferred process, the acid, aqueous solution of the sulfonation product is extracted with a solution of a water-insoluble amine in a water-insoluble organic solvent. In this way there are obtained sulfonated arylphosphines which are substantially free of the Lewis acids added in the sulfonation step. This method has proven particularly useful when using boric acid as Lewis acid.

In detail, in this method, the sulfonation mixture is admixed while maintaining the above-mentioned temperatures with the amount of water required to dilute the sulfuric acid present to 0.5% to 50% by weight, preferably 25% to 35% by weight. To the diluted solution is added the water-insoluble amine dissolved in a water-insoluble organic solvent. The concentration of the amine in solution is from 1.0% to 35% by weight, preferably from 10% to 30% by weight, and most preferably 13% to 25% by weight, in each case based on the solution.

From 0.5 to 3.0 mol, preferably from 0.5 to 2.5 mol, of amine are used per equivalent of sulfonic acid. The use of excess amine ensures that only small phosphine losses occur. An amine excess higher than that given above is possible, but does not lead to improvement in the separation or purification operation or in the yield.

After intensive mixing, two phases are formed. The aqueous phase, which has a higher specific gravity, contains the sulfuric acid and almost all of the Lewis acid; the organic phase, which is low in sulfate and almost free of Lewis acid, contains the amine salt of the sulfonated phosphine dissolved in the organic solvent. The two phases are separated from one another. The organic phase is reacted with a solution of an inorganic base in water. The base is used in an amount approximately equivalent to the amount of dissolved amine salt. Excess base should be avoided because it contaminates the end product. In this way the aqueous solution of the sulfonated arylphosphine is obtained with recovery of the water-insoluble amine; the recovered amine is available for further use.

The process described can be carried out either batchwise or continuously. Conventional material separation equipment, such as countercurrent extraction units, is satisfactory for this purpose.

Instead of adding the base dissolved in water all at once to the solution of the amine salt in the organic medium, the addition may, according to a preferred embodiment, be made in portions. This method is successfully used especially when it is desired to separate a sulfonation mixture which contains products of various sulfonation stages.

Suitable water-insoluble amines used for carrying out the process include those which are water-insoluble homo- and heterocyclic, aliphatic, aromatic, and araliphatic. Preferably, the amines are open-chain, branched or unbranched aliphatic amines and have 10 to 60, especially 13 to 36, carbon atoms. Less well suited are amines whose salts with the sulfonic acids are insoluble or soluble only to a limited extent in the organic solvent. Examples of particularly useful amines are tri-n-octylamine, triisooctylamine, tri-2-ethylhexylamine, and tridodecylamine.

The amines are dissolved in a water-insoluble organic solvent. Examples of suitable solvents are aliphatic or aromatic hydrocarbons or hydrocarbon mixtures, for example toluene, kerosene, alcohols having 4 to 20 carbon atoms, and ethers having 8 to 20 carbon atoms. Suitable bases for transferring the sulfonated phosphines to the aqueous phase are hydroxides of alkali and alkaline earth metals, in particular alkali metal hydroxide, ammonia, and alkali metal carbonates.

The recovery is advantageously carried out from room temperature to about 40° C. Higher temperatures may be used, but give no advantages. The statements about the solubility of the amine and the organic solvent in water are, in each case, based on the temperatures at which the process is carried out. The end product is either left in the aqueous solution or isolated in solid form, for example, by evaporation, crystallization, decantation, or filtration.

The novel process is illustrated in the following examples, but it is not limited to the embodiments exemplified.

EXAMPLE 1

Sulfonation of triphenylphosphine 5.0 g (81 mmol) of commercial boric acid is dissolved, with stirring, in 50 ml of concentrated sulfuric acid at room temperature in a two-neck flask fitted with dropping funnel. The mixture is stirred further for about 30 minutes in vacuo, and argon gas is subsequently introduced. In this way, oxidizing gases dissolved in the acid mixture are completely removed. The mixture is cooled to 0° C., 15 g (57 mmol) of triphenylphosphine is added, and the flask is again evacuated. After 15 minutes the phosphine has completely dissolved. Subsequently, under an argon atmosphere, 250 ml of oleum (65% by weight $SO_3$) is added dropwise at about 6 ml/min and a maximum temperature of the reaction mixture of 10° C. After the addition is complete, the mixture is allowed to slowly warm to room temperature and is stirred for a further 10 days. If the reaction mixture solidifies because of the high $SO_3$ content it can be heated for up to 2 days to a temperature not exceeding 43° C.

For the recovery, the reaction mixture is poured, in an argon atmosphere, onto ice in a 3 liter Büchner funnel or a glass frit. A 10 liter round-bottom flask serves as the receiver. The whole apparatus is evacuated beforehand for 10 minutes and the ice is thereby degassed.

To avoid overheating, care must be taken to insure that the oleum always drops onto ice and not directly onto water. For this purpose, the level of the aqueous hydrolysate in the funnel (or in the frit) can be lowered at regular time intervals by creating a vacuum in the receiver flask. When the entire mixture is hydrolyzed, the funnel (or the frit) is washed thoroughly with 25% sodium hydroxide solution and the strongly acid solution in the receiver is neutralized with cooling and intensive stirring. The solution is then evaporated in vacuo in a water bath until considerable amounts of sodium sulfate precipitate. Two liters of methanol are added to this suspension while stirring intensively and the precipitated sodium sulfate is subsequently filtered out. The filter residue is washed three times with 150 ml of methanol each time and the combined filtrates are evaporated to dryness. The residue is then dissolved in a minimum (about 30 ml) of water and the solution is syringed while stirring into 250 ml of methanol. Precipitated sodium sulfate is again filtered out and the solution is evaporated to dryness in vacuo.

The results of the experiments are summarized in Table I; Experiments 1 to 3 were carried out with the addition of boric acid, Experiments 4 to 6 omitted the boric acid.

TABLE I

| Sulfonation of triphenylphosphine | | | | | |
|---|---|---|---|---|---|
| Experiment No. | $SO_3$ in $H_2SO_4$ (% by wt.) | Temp. | Reaction time | Oxide formation | Proportion of tri-substituted phosphine (%) |
| 1 | 42 | RT* | 72 h | none | 50 |
| 2 | 42 | RT | 24 h | none | 50 |
| 3 | 65 | RT,48h: 43° C. | 18 d | none | 85 |
| 4 | 40 | RT | 42 h | considerable | <10 |
| 5 | 65 | RT | 18 h | moderate | ca. 20 |
| 6 | 65 | RT | 72 h | complete | <5 |

*RT = room temperature

The experiments show that, in the presence of boric acid, there is no formation of oxide at room temperature, 42% by weight of $SO_3$ in the oleum and a reaction time of 72 hours (Experiment 1). However, under similar conditions, without boric acid, considerable amounts of oxide are formed after only 42 hours (Experiment 4). Even more drastic are the differences when using oleum containing 65% by weight of $SO_3$. Even after a reaction time of 18 days, 2 days of which are at 43° C. there is no formation of oxide in the presence of boric acid (Experiment 3); in comparison, the starting material is completely oxidized after only 72 hours in the absence of boric acid.

EXAMPLE 2

Sulfonation of 2,2'-bis(diphenylphosphinomethyl)-1,1'-binaphthalene (NAPHOS)

5.0 g (81 mmol) of boric acid is dissolved, with stirring, in a 50 ml of concentrated sulfuric acid at room temperature in a two-neck flask fitted with dropping funnel. The mixture is stirred further for about 30 minutes in vacuo and argon gas is subsequently introduced.

In this way oxidizing gases dissolved in the acid mixture are completely removed. The mixture is then cooled to 0° C., 7.5 g of NAPHOS (11.5 mmol) is added, and the flask is again evacuated. After about 15 minutes the phosphine has dissolved completely. Subsequently, under an argon atmosphere, 150 ml of oleum (65% by weight $SO_3$) is added dropwise at about 3 ml/min and a maximum temperature of the reaction mixture of 10° C. After the addition is complete, the mixture is allowed to slowly warm to room temperature and is stirred for a further 60 hours. If the reaction mixture solidifies because of the high $SO_3$ content, the mixture can be heated for a short time to 35° C. to ensure thorough mixing.

For the recovery, the reaction mixture is poured, in an argon atmosphere, onto ice in a 3 liter Büchner funnel or a glass frit. A 10 liter round-bottom flask serves as the receiver. The whole apparatus is evacuated for 10 minutes and the ice is thereby degassed. To avoid overheating, care must be taken to ensure that degassed. To avoid overheating, care must be taken to ensure that the oleum always drops onto ice and not directly onto water. For this purpose, the level of the aqueous hydrolysate in the funnel (or on the frit) can be lowered at regular intervals by creating a vacuum in the receiver flask. When the entire mixture is hydrolyzed, the funnel (or the frit) is washed thoroughly with 25% sodium hydroxide solution and the strongly acid solution in the receiver is neutralized with cooling and intensive stirring. The solution is then evaporated in vacuo in a water bath until considerable amounts of sodium sulfate precipitate. 1 liter of methanol is added to this suspension while stirring intensively, and the sodium sulfate precipitated in large amounts is subsequently filtered out. The filter residue is washed three times with 75 ml of methanol each time and the combined filtrates are evaporated to dryness. The residue is then dissolved in a minimum amount (about 15 ml) of water and the remaining sodium sulfate is removed by means of gel chromatography on Sephadex G-15.

The results are shown in Table II.

TABLE II

| | Sulfonation of NAPHOS | | | |
|---|---|---|---|---|
| Experiment | $SO_3$ in $H_2SO_4$ (% by wt.) | Temp. | Reaction time (h) | Oxide formation |
| 1 | 25 | 43° C. | 12 | none |
| 2 | 25 | 70° C. | 24 | complete |
| 3 | 60 | RT* | 60 | 5% |
| 4 | 40 | RT | 96 | 5% |
| 5 | 25 | 43° C. | 12 | 15% |
| 6 | 25 | 43° C. | 48 | 25% |

*RT = room temperature

EXAMPLE 3

A) Sulfonation of NAPHOS 200 g of concentrated sulfuric acid is charged under a nitrogen atmosphere into a 1 liter flask fitted with stirrer, thermometer, dropping funnel, and condenser, and admixed with 26.1 g (422.3 mmol) of boric acid. After complete dissolution of the solid, 27.7 g (42.6 mmol) of NAPHOS is added to the solution. The mixture is stirred for 1 hour at room temperature and subsequently 550.7 g (4474 mmol) of oleum (65%) is added dropwise over 30 minutes. The homogeneous reaction mixture is then stirred for 72 hours at room temperature.

For the recovery, the sulfonation mixture (804.5 g) is added, under nitrogen atmosphere, to a 6 liter flask containing 3195.1 g of water at about 10° C. During the addition, the internal temperature is maintained between 15° and 25° C. by intensive cooling. The hydrolysis mixture (3999.6 g) containing 0.65% (420.7 mmol) of boric acid is subsequently extracted with different mixtures of triisooctylamine (TIOA) and toluene.

b) Extraction 950 g of the hydrolysis mixture containing 99.9 mmol of boric acid is extracted for 2 hours at room temperature with the amounts of TIOA/toluene described in Table III.

TABLE III

| Experiment | TIOA (g) | Toluene (g) | TIOA/toluene (parts by weight) | TIOA/NAPHOS* (mol) |
|---|---|---|---|---|
| 3.1 | 53.6 | 536.0 | 1:10 | 15:1 |
| 3.2 | 53.6 | 375.2 | 1:7 | 15:1 |
| 3.3 | 53.6 | 214.4 | 1:4 | 15:1 |
| 3.4 | 35.7 | 357.0 | 1:10 | 10:1 |

*NAPHOS: Starting material for BINAS (sulfonated 2,2'-bis(diphenylphosphinomethyl)-1-1'-biphenyl)

The aqueous waste acid phases obtained after phase separation have the following boric acid contents (Table IV).

TABLE IV

| | Waste acid | Boric acid | |
|---|---|---|---|
| Experiment | (g) | (mmol) | (% of I*) |
| 3.1 | 926.1 | 99.3 | 99.4 |
| 3.2 | 926.1 | 98.3 | 98.4 |
| 3.3 | 926.0 | 97.9 | 98.0 |
| 3.4 | 931.4 | 98.8 | 98.9 |

*I: amount of boric acid used

EXAMPLE 4

In accordance with the method of Example 3, 10.1 g (15.5 mmol) of NAPHOS and 7.6 g (123 mmol) of boric acid are dissolved in 66.8 g of concentrated sulfuric acid and subsequently admixed with 221.5 g (1800 mmol) of oleum (65%). After 2 hours' reaction time at room temperature, the sulfonation mixture (306.0 g) is hydrolyzed with 1300.0 g of water; the boric acid content of the hydrolysis mixture (1606.0 g) is 0.47% (122 mmol).

The hydrolysis mixture is extracted for 1 hour at room temperature with a solution of 82.1 g (233 mmol) of TIOA in 821.0 g of toluene. The waste acid phase obtained after phase separation contains 7.4 g (120 mmol) of boric acid.

The organic phase is gradually admixed with 1.5% sodium hydroxide solution while the pH is simultaneously measured with a commercial glass electrode. The aqueous sodium salt solution of the sulfonation mixture obtained in the pH range up to 3.5 is separated off and discarded. The desired product fraction obtained in the pH range of 3.5 to 11.1 and containing 0.22 mmol of boric acid can be used without further purification as a component of a catalyst system for hydroformylation.

EXAMPLE 5

Example 4 was repeated except that the reaction time is 6 hours, yielding 1606.0 g of hydrolysis mixture containing 0.47% (122 mmol) of boric acid.

After recovery as in Example 4, the waste acid phase contains 7.5 g (121 mmol) of boric acid. Just 0.14 mmol of boric acid is found in the desired product fraction (pH range from 3.5 to 11.1).

EXAMPLE 6 a) Sulfonation of triphenylphosphine 1281.0 g (4.00 mol of $SO_3$) of oleum (25%) is charged under a nitrogen atmosphere into a 1 liter flask fitted with a stirrer, thermometer, dropping funnel, and condenser, and admixed with 79.1 g (1.28 mol) of boric acid. After complete dissolution of the solid, 83.6 g (0.32 mol) of triphenylphosphine is added to the solution. The homogeneous reaction mixture is stirred for 48 hours at room temperature.

For the recovery, the sulfonation mixture (1443.7 g) is added under nitrogen atmosphere to a 6 liter flask containing 2866.2 g of water at about 10° C. During the addition, the internal temperature is maintained between 15° and 25° C. by intensive cooling. The hydrolysis mixture (4309.9), containing 1.8% (1276 mmol) of boric acid, is subsequently extracted with different mixtures of TIOA and toluene.

b) Extraction 800 g of hydrolysis mixture containing 237 mmol of boric acid is extracted for 1 hour at 40° C. with the amounts of TIOA/toluene described in Table V.

TABLE V

| Experiment | TIOA (g) | Toluene (g) | TIOA/toluene (parts by weight) | TIOA/TPP (mol) |
|---|---|---|---|---|
| 6.1 | 75.8 | 303.4 | 1:4 | 1:3.6 |
| 6.2 | 94.8 | 379.2 | 1:4 | 1:4.5 |
| 6.3 | 75.8 | 530.6 | 1:7 | 1:3.6 |
| 6.4 | 75.8 | 758.0 | 1:10 | 1:3.6 |

The aqueous waste acid phases obtained after phase separation have the following boric acid contents (Table VI).

TABLE VI

| Experiment | Waste acid (g) | Boric acid (mmol) | Boric acid (% of I) |
|---|---|---|---|
| 6.1 | 753.5 | 225 | 94.9 |
| 6.2 | 753.6 | 226 | 95.4 |
| 6.3 | 755.7 | 228 | 96.2 |
| 6.4 | 756.9 | 230 | 97.0 |

I = % of boric acid used

What we claim is:

1. A process for sulfonation with oleum of at least one starting arylphosphine selected from the group consisting of mono-, di-, oligo-, and polyphosphines, said process comprising carrying out said sulfonation at a sulfonation temperature of 0° to 80° C. in the presence of at least one Lewis acid to form a sulfonation mixture containing at least one sulfonated arylphosphine.

2. The process of claim 1 wherein said temperature is 10° to 50° C.

3. The process of claim 1 wherein said oleum is added to a starting solution of said starting arylphospine and said Lewis acid in concentrated sulfuric acid.

4. The process of claim 3 wherein said temperature is 10° to 50° C.

5. The process of claim 1 wherein said Lewis acid is a boron compound.

6. The process of claim 5 wherein said boron compound is boric acid.

7. The process of claim 1 wherein said Lewis acid is present in at least an equimolar amount based on P(III) atoms contained in said starting arylphosphine.

8. The process of claim 3 wherein said starting solution is saturated with boric acid.

9. The process of claim 1 wherein said sulfonation mixture is diluted with water to form an aqueous solution, said aqueous solution is extracted with a separating solution of at least one water-insoluble amine in a water-insoluble organic solvent to form a first aqueous phase and a first organic phase, said first organic phase is separated from said first aqueous phase and brought into contact with an aqueous solution of a base to form a second aqueous phase and a second organic phase said second aqueous phase is separated from said second organic phase along with said sulfonated arylphosphine.

10. The process of claim 9 wherein there is 0.5 to 3 mol of said water-insoluble amine per chemical equivalent of sulfonic acid.

11. The process of claim 9 wherein said sulfonation mixture is diluted so that sulfuric acid is present in a dilution amount of 0.5% to 50% by weight, based on said aqueous solution at a dilution temperature of 0° to 40° C.

12. The process of claim 11 wherein said dilution amount is 25% to 35% by weight and said dilution temperature is 0° to 20° C.

13. The process of claim 10 wherein there is 0.5 to 2.5 mol of said amine are used per chemical equivalent of said sulfonic acid.

14. The process of claim 9 wherein said water-insoluble amine constitutes an amine amount of 1.0% to 35% by weight, based on said separating solution.

15. The process of claim 14 wherein said amine amount is 10% to 30% by weight, based on said separating solution.

16. The process of claim 15 wherein said amine amount is 13% to 25% by weight, based on said separating solution.

17. The process of claim 9 wherein said water-insoluble amine is a branched or unbranched, open chain aliphatic amine having 10 to 60 carbon atoms.

18. The process of claim 17 wherein said water-insoluble amine has 13 to 36 carbon atoms.

19. The process of claim 18 wherein said water-insoluble amine is selected from the group consisting of tri-n-octyl amine, triisooctylamine, diisoctylamine, tri-2ethylhexylamine, and tridodecylamine.

20. The process of claim 9 wherein said organic solvent is selected from the group consisting of aliphatic hydrocarbons, aromatic hydrocarbons, and mixtures thereof.

21. The process of claim 20 wherein said organic solvent is selected from the group consisting of toluene, kerosene, and mixtures thereof.

* * * * *